(12) United States Patent
Lazor

(10) Patent No.: US 10,624,788 B2
(45) Date of Patent: Apr. 21, 2020

(54) FACE MASK WITH HEAD SUPPORT

(71) Applicant: John B. Lazor, Westwood, MA (US)

(72) Inventor: John B. Lazor, Westwood, MA (US)

( * ) Notice: Subject to any disclaimer, the term of this patent is extended or adjusted under 35 U.S.C. 154(b) by 259 days.

(21) Appl. No.: 15/414,347

(22) Filed: Jan. 24, 2017

(65) Prior Publication Data

US 2017/0209309 A1 Jul. 27, 2017

Related U.S. Application Data

(60) Provisional application No. 62/286,680, filed on Jan. 25, 2016.

(51) Int. Cl.
*A61F 9/04* (2006.01)
*A47C 7/38* (2006.01)

(52) U.S. Cl.
CPC ................ *A61F 9/04* (2013.01); *A47C 7/383* (2013.01)

(58) Field of Classification Search
CPC .......... A61F 9/04; A61F 9/045; A61F 13/124; A61F 13/122; A41G 7/00; A47C 7/38; A47C 7/383; A41D 13/1169; A41D 13/0556; A41D 13/0568; A41D 13/11; A41D 13/1107; A41D 13/1184; A41D 13/1176; A41D 20/00; B60R 22/001; B60R 22/12; B60R 2022/028; B60N 2/879; B60N 2/882; B60N 3/00; B64D 11/062
See application file for complete search history.

(56) References Cited

U.S. PATENT DOCUMENTS

| | | | | |
|---|---|---|---|---|
| 4,122,847 A * | 10/1978 | Craig | ..................... | A61F 9/026 128/858 |
| 4,339,151 A * | 7/1982 | Riggs | ..................... | A47C 7/383 128/857 |
| 4,411,263 A * | 10/1983 | Cook | ........................ | A61F 9/04 128/858 |
| 4,872,217 A | 10/1989 | Kitayama | | |
| 5,360,393 A * | 11/1994 | Garth | .................. | A61F 5/05883 128/870 |
| 6,266,825 B1 * | 7/2001 | Floyd | ..................... | A47C 7/383 2/311 |
| 6,607,245 B1 * | 8/2003 | Scher | ..................... | A47C 7/383 297/393 |
| 7,202,774 B2 | 4/2007 | Hoyle | | |
| 2004/0124685 A1 * | 7/2004 | Buch | ........................ | B60N 3/00 297/393 |

(Continued)

FOREIGN PATENT DOCUMENTS

WO WO-0206881 A2 * 1/2002 ............... A61F 9/04

*Primary Examiner* — Amy Vanatta
(74) *Attorney, Agent, or Firm* — Mintz Levin Cohn Ferris Glovsky and Popeo, P.C.

(57) ABSTRACT

Methods and devices are provided for supporting a person's head. Generally, a face mask is provided having an eye piece sized to fit a human face and having left and right side straps. The eye piece has a left side portion and right side portion that each have a concavity formed therein that is configured to be positioned around a user's eye. The left and right side straps each have a first end that is attached to the left and right side portions of the eye piece, respectively. A reusable adhesive can be coated onto at least a portion of each of the left and right side straps, which can allow the side straps to each be repeatedly and removably attached to a support structure.

20 Claims, 4 Drawing Sheets

(56) References Cited

U.S. PATENT DOCUMENTS

| | | | |
|---|---|---|---|
| 2008/0251085 A1* | 10/2008 | Schwebel | A61F 9/04 128/858 |
| 2009/0255026 A1* | 10/2009 | Benner | A61F 9/04 2/12 |
| 2009/0271904 A1* | 11/2009 | Bentley | A41D 20/00 2/15 |
| 2014/0041091 A1 | 2/2014 | Sternlight | |
| 2016/0324243 A1* | 11/2016 | Jackson | A41G 7/00 |
| 2017/0050547 A1* | 2/2017 | Dunham | B60N 2/882 |
| 2017/0135861 A1* | 5/2017 | Sternlight | B60N 2/882 |
| 2018/0002021 A1* | 1/2018 | Smith | B60N 2/882 |

* cited by examiner

FACE MASK WITH HEAD SUPPORT

CROSS REFERENCE TO RELATED APPLICATIONS

This application claims priority to U.S. Provisional Application No. 62/286,680 filed on Jan. 25, 2016 and entitled "Face Mask with Head Support," which is hereby incorporated by reference in its entirety.

FIELD

A face mask with a head support and methods for using the same are provided.

BACKGROUND

Face masks and travel pillows are commonly used by travelers or people seeking a better resting experience. Consequently, significant development has gone into a range of products targeted at travelers. These products include pillows that extend around a user's neck to support their head, and face masks that are designed to block light from a user's eyes and that extend around a seat headrest to support a user's head while the user rests.

However, the pillows tend to be bulky and the face masks either only extend around the user's head, thus allowing the user to slump sideways while the user attempts to rest in a seat, or require the user to wrap the mask around the seat headrest of the seat in which the user is resting, resulting in potential size issues. Extending a face mask strap around a seat headrest may also bother or interfere with anyone seated behind a user. Additionally, many face masks attach to a user's forehead, putting an unnatural strain on the user's head during use.

Accordingly, there remains a need for methods and devices for supporting a user's head in an agronomical position, especially while traveling.

SUMMARY

Various methods and devices are provided for a face mask with head support.

In one aspect, a face mask is provided with an eye piece, a left side strap, and a right side strap. The eye piece has a left side portion, a right side portion, and a middle portion formed therebetween and configured to extend around a user's nose. The left and right side portions each having a concavity formed therein that is configured to be positioned around a user's eye. The left side strap has a first terminal end mated to the left side portion of the eye piece and has a second terminal end. The right side strap has a first terminal end mated to the right side portion of the eye piece and has a second terminal end. In an exemplary embodiment, a reusable adhesive is coated onto at least a portion of the second terminal end of the left and right side straps so that the second terminal ends of the left and right side straps can be repeatedly and removably mated to a support structure.

The face mask can vary in any number of ways. For example, the left and right side straps can be attached to the left and right side portions of the front eye piece along a central longitudinal axis extending centrally through the concavity in each of the left and right side portions such that the left and right side straps are configured to be aligned with a user's eyes when the left and right side portions are disposed over a user's eyes. As another example, the left and right side portions can each have a substantially oblong region extending around a perimeter of the concavity, and each oblong region can have a thickness that is greater than a thickness of the concavity. For another example, the front eye piece can be formed from a compressible material. In another example, the concavity in each of the left and right side portions can have an opening formed therein for allowing a user to see through the front eye piece.

In another embodiment, the middle portion of the front eye piece can have a bridge portion formed therein and shaped to contour a human nose. As another example, the concavity can extend in a forward direction relative to a front eye piece and the reusable adhesive is coated on a back side of each strap. Each side strap can include a reusable cover removably disposed over the reusable adhesive coating. Each reusable cover can include an elongate member having a first end fixedly attached to the side strap.

In another aspect, a face mask is provided that has a front eye piece and left and right side straps. The front eye piece is sized to fit a human face. The left and right side straps are attached to opposite left and right sides of the front eye piece. Each side strap has a reusable adhesive formed on a back surface thereof. Each side strap also has a length that is greater than a length of the front eye piece such that the left and right side straps are configured to attach to corresponding sides of a seat headrest when a user is wearing the front eye piece and when a head of the user is positioned adjacent to the seat headrest.

The face mask can vary in any number of ways. For example, the front eye piece can include a left side portion with an oblong rim shaped to extend around a left eye of a human face, and a right side portion with an oblong rim shaped to extend around a right eye of a human face. As another example, the left and right side portions can include concavities formed therein. Each concavity can be surrounded by the oblong rim, and each concavity can have a depth sufficient to prevent contact between the concavity and a user's eye. For another example, the front eye piece can bulge outward at a location of each eye on a human face.

In another embodiment, the front eye piece can have openings at a location of each eye on a human face. The front eye piece can have a mid-portion that is contoured to match a human nose. As another example, the reusable adhesive on each side strap can be coated on an end of each side strap opposite to an end of each side strap attached to the front eye piece. In another example, each side strap can have a reusable cover removably disposed over the reusable adhesive coating.

In another aspect, a method of using a face mask is provided including placing a front eye piece of the face mask over a user's eyes. The method also includes attaching two side straps of the face mask to corresponding sides of a seat headrest by a reusable adhesive disposed on an inner surface of each side strap.

The method can be varied in a variety of ways. For example, the two side straps can be aligned with a central axis extending across the user's eyes. The method can also include, before attaching the two side straps, removing a cover disposed over the reusable adhesive on each side strap.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
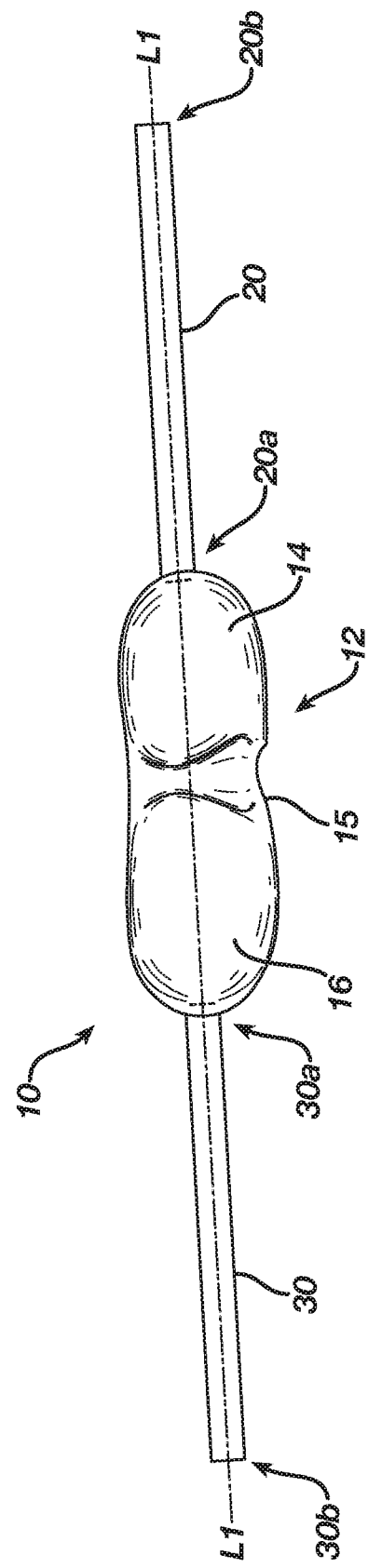
FIG. 1 is a front view of a face mask with an eye piece and first and second side straps.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for securing a user's head to a seat. Generally, a face mask can be provided with an eye piece and left and right side straps. The eye piece can have a left side portion and right side portion. The left and right side portions can each have a concavity formed in the portions that is configured to be positioned around a user's eye. The concavities can act to keep pressure off of the eyes of the user by preventing the eye piece from contacting the user's eyes and/or the user's eyelashes to provide a more comfortable fit. A middle portion can be formed between the left and right side portions to extend around a user's nose. The middle portion can allow greater comfort when the face mask is worn by a user by allowing the face mask to sit flush around the user's eyes without being lifted or incorrectly positioned because of the face mask's interaction with the user's nose. The left and right side straps can each have a first terminal end that is attached to the left and right side portions of the eye piece, respectively. The side straps can each also have a second terminal end. The side straps can be attached to the to the eye piece so that the face mask applies support to the user at eye level rather than along the user's forehead. This positioning allows the face mask to be configured ergonomically to pull at eye level to hold the user's head in a proper, more natural orientation. The face mask is therefore more comfortable and convenient to wear. A reusable adhesive can be coated onto at least a portion of the second terminal end of each of the left and right side straps, which can allow the side straps to each be repeatedly and removably attached to a support structure or surface. The side straps can attach to the front or the sidewalls of virtually any seat and do not extend around the back of the seat, which prevents the straps from interfering with anyone behind the seat. The face mask can come in a variety of sizes. For example, illustrative embodiments of the face mask can be small, medium, and large sizes to accommodate a variety of sizes of heads and faces. Illustrative embodiments of the face mask can also come in an adult size and a child size to accommodate an adult's face or a child's face.

Figure 2:
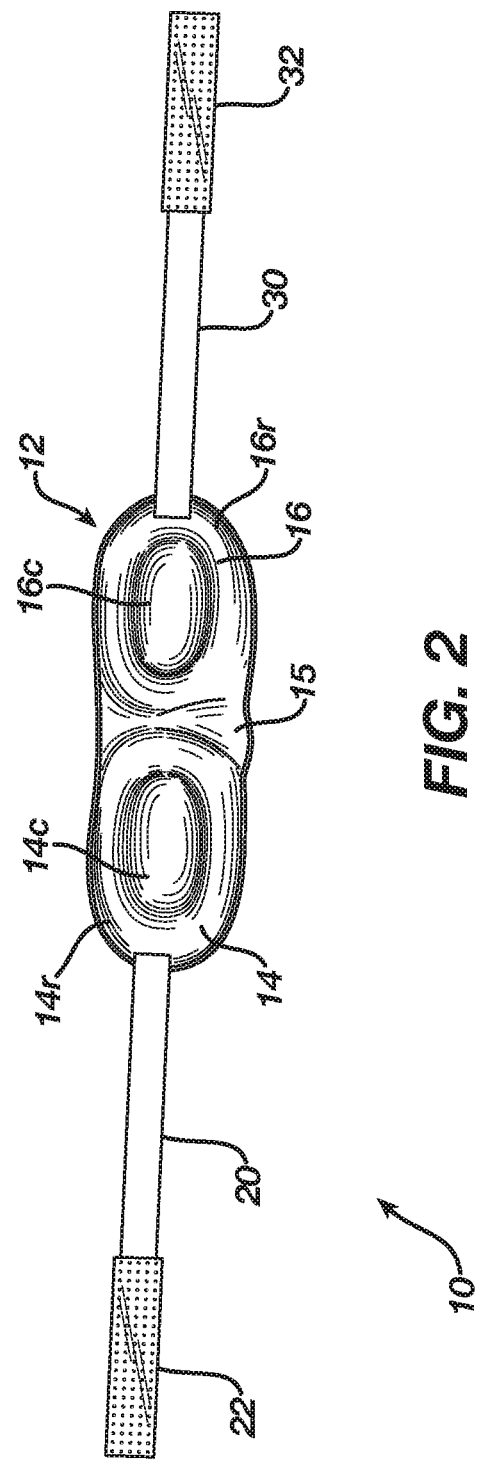
FIG. 2 is a rear view of the face mask of FIG. 1 showing adhesive coatings with removable covers on the straps.

FIG. 1 illustrates one embodiment of a face mask with head support. As shown in FIG. 1, the illustrated face mask 10 generally has an eye piece 12, a left side strap 20, and a right side strap 30. The eye piece 12 includes a left side portion 14 and a right side portion 16. The eye piece can be provided in a variety of sizes. In one exemplary embodiment, the face mask has a size of about 9 inches (23 cm) in width by about 3.25 inches (8.2 cm) in height. The left and right side portions can have a variety of forms and sizes. As illustrated in FIG. 2, the side portions 14, 16 each have a concavity 14c, 16c formed to be positioned over a user's eyes. The concavities 14c, 16c extend or bulge in a forward direction from the face mask 10, away from a user's face. A middle portion 15 is formed between the left and right side portions 14, 16 and is shaped to extend around the user's nose.

Figure 4:
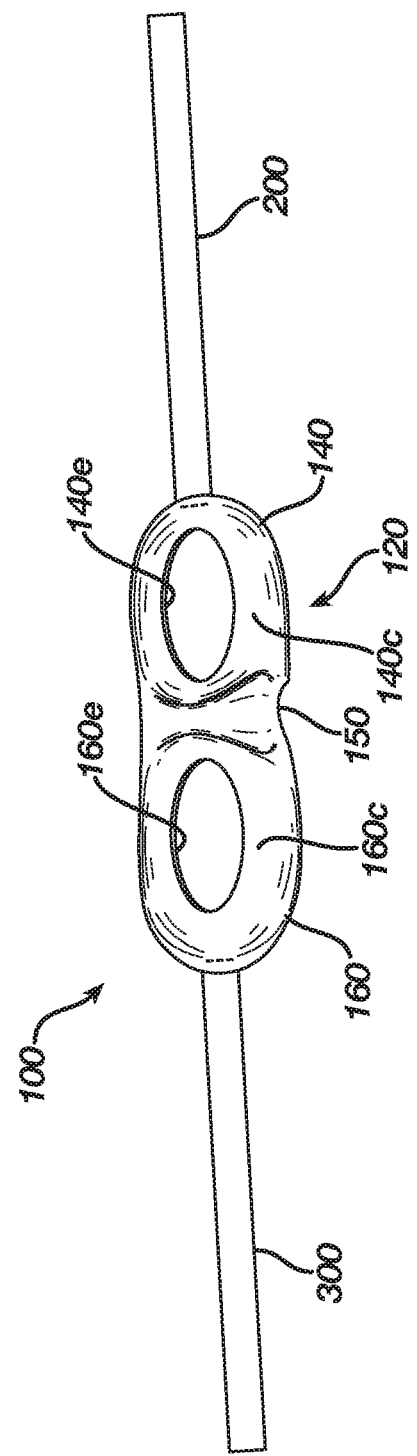
FIG. 4 is a front view of another embodiment of a face mask with an eye piece having eye openings therein and two side straps.

The left and right portions of the eye piece can be varied in a number of different ways. For example, the left and right portions 14, 16, as illustrated in FIG. 2, have a region around a perimeter of each of the concavities 14c, 16c that is thicker than the concavities 14c, 16c, allowing for greater comfort and helping to prevent the concavities 14c, 16c from putting uncomfortable pressure on the eyes of the user or contacting the eyelids of the user. The region can be substantially oblong in shape, as illustrated, or can take other shapes to complement an overall shape of the eye piece. In other embodiments, the left and right portions can also have openings formed on the concavities so that a user can look out of the face mask during use. As illustrated in FIG. 4, an illustrated face mask 100 is similar to the face mask 10 and has an eye piece 120, a left side strap 200, and a right side strap 300. The eye piece 120 includes a left side portion 140 and a right side portion 160, each having a concavity 140c, 160c formed to be positioned over a user's eyes, and a middle portion 150 formed between the left and right side portions 140, 160. Openings 140e, 160e are formed on the concavities 140c, 160c, respectively, positioned over the eyes of the user. The user can thus benefit from both the support and rest that the face mask can provide when the face mask is attached to a surface and can also benefit from being able to see while wearing the face mask.

The middle portion can also be varied in a variety of ways. As illustrated in FIG. 1, the middle portion 15 extends from the eye piece 12 and has a generally triangular shape to act as a bridge to contour the shape of a human nose, providing a more comfortable wearing experience for the user. In other embodiments, the middle portion can have a cut-out portion that is shaped to allow a human nose to extend from the eye piece without making extensive contact with the face mask.

The left and right side straps can take a variety of forms and a variety of sizes. For instance, the side strap can be about 10 inches by about 0.75 inches or about 30 cm by about 1.9 cm. As an illustrative embodiment, each of the left and right side straps 20, 30 shown in FIG. 1 has a first terminal end 20*a*, 30*a* attached to the left and right side portions 14, 16, respectively. As shown in FIG. 2, on a second terminal end 20*b*, 30*b* opposite to the first terminal end 20*a*, 30*a*, the left and right side straps 20, 30 have reusable adhesive coatings 22, 32, respectively. The adhesive coatings can be any adhesive that can be used to repeatedly and removably attach the left and right side straps to a structure, for example a low-tack pressure-sensitive adhesive such as elastomeric copolymer microspheres. The adhesive coatings can cover at least a portion of the side straps. The adhesive coatings can have a variety of sizes and shapes, such as about 3.5 inches by about 0.75 inches or about 8.9 cm by about 1.9 cm. As illustrated in FIG. 2, the adhesive coatings 22, 32 extend along a portion of the second terminal portion of each of the side straps 20, 30. However the adhesive coatings can cover any or all of the side straps. The adhesive coatings 22, 32 are coated on the back sides of each strap 20, 30, but the adhesive coatings can be placed on either side of the straps depending on the desired use of the face mask. The adhesive coatings can be affixed to any support structure or surface, such as a headrest of a seat. The adhesive coatings allow the face mask to be affixed to a surface during use and then removed from the surface for later reuse, allowing a user to cover his or her eyes with the face mask and attach the side straps to a surface to keep the user's head in a comfortable but secure position while the user rests. The adhesive coatings also allow the face mask to be attached to a variety of surfaces. For example, the adhesive surface can allow the face mask to be attached to the side of an airplane headrest while in use, allowing the user to use the face mask to sleep or rest without slumping in the airplane seat. The adhesive coatings also allow the user to attach the face mask at a location and a distance from the surface that is most comfortable for each individual user without having to resize any straps or design particular face masks for particular headrest styles.

Lengths of the side straps can also vary. The illustrated side straps 20, 30 are longer than a length of the eye piece 12, allowing the straps to attach to sides of a wider seat, such as an airplane seat, when the face mask 10 is positioned over the user's face and attached to a surface behind the user's head. However, any length can be used. A material of the left and right side straps can vary, as well. In one embodiment, the side straps 20, 30 can be made of an elastic material designed to stretch and flex to provide a snug but comfortable fit between the user and the surface on which the side straps 20, 30 are attached. However, any material can be used, including non-elastic materials.

Figure 3:
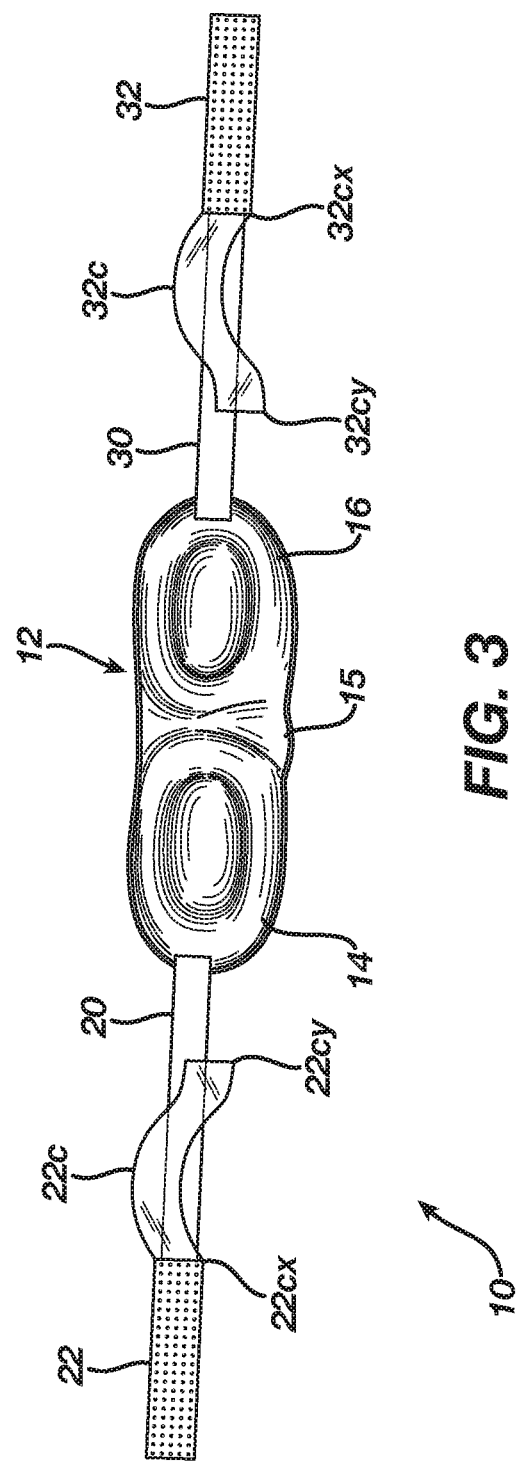
FIG. 3 is a rear view of the face mask of FIG. 1 showing the covers of FIG. 2 peeled back to expose the adhesive coatings.

The left and right side straps can also include covers for the adhesive coatings. As illustrated in FIGS. 2 and 3, the side straps 20, 30 have covers 22*c*, 32*c* for covering the adhesive coatings 22, 32. The covers can protect the adhesive coatings and extend the life of the adhesive property of the adhesive coatings while preventing the adhesive coatings from sticking to surfaces other than a desired surface. The covers can take a variety of forms as long as the covers are able to cover the adhesive coatings. As illustrated in FIGS. 2 and 3, the covers 22*c*, 32*c* can be formed from elongate sheet-like members. The covers can be attached to the side straps or free from the side straps. As shown in FIG. 3, the covers 22*c*, 32*c* have a first end 22*cx*, 32*cx* that is attached to the side straps 22, 32, respectively, between the adhesive coatings 22, 32 and the eye piece 12, allowing the opposite end 22*cy*, 32*cy* of the covers 22*c*, 32*c* to be peeled away. However, the covers can be attached at any point along the side straps.

The left and right side straps can be positioned and attached to the eye piece at a variety of locations. As illustrated in FIG. 1, the left and right side straps 20, 30 are aligned with the eye piece 12 along a central longitudinal axis L1 that extends through the concavities 14*c*, 16*c* in the left and right side portions 14, 16. The longitudinal axis L1 is aligned with the intended location of a user's eyes. Thus, attaching the side straps 20, 30 along the central longitudinal axis L1 allows the straps 20, 30 to be aligned with the user's eyes, thus applying a pulling force to the user's head at a location that is level with the user's eyes rather than higher on the forehead of the user. This alignment keeps the head of the user in a more natural and ergonomic position while the user rests with the face mask, thus providing a more comfortable experience for the user.

The eye piece can be made from a variety of materials suitable for use as an eye mask, such as nylon or cotton. The eye piece can have a cover and an inner portion. The cover and the inner portion can be the same material or different materials. The material can be thick enough to block light to assist in the user's rest, and the material can also be opaque or translucent. The material can be a compressible material to allow for easier storage and greater comfort, such as foam.

In an exemplary embodiment, a user places the eye piece 12 of the face mask 10 over his or her eyes. The user attaches the side straps 20, 30 to corresponding sides of a seat headrest. The straps can be attached to any location that is most comfortable for the user, such as on the side of the headrest. The user can attach the side straps 20, 30 to the side of an airplane headrest, but the user can attach the face mask in other locations, too. The user can attach the side straps to any seat with a backrest to which to secure the straps. The user can attach the side straps 20, 30 by a reusable adhesive disposed on an inner surface of each side strap 20, 30. The user can remove the cover 22*c* disposed over the reusable adhesive on each side strap 20, 30 before attaching the side straps 20, 30 to a desired surface. The user may position and/or the eye piece 12 on the user's face and the side straps 20, 30 on the headrest to ensure that the face mask is comfortably positioned on the user's face and provides sufficient support for the user's head. In one exemplary embodiment, the side straps 20, 30 can be aligned with a central axis extending across the user's eyes, which causes force to be applied across the eyes instead of along the user's forehead. The user experiences a more ergonomic head position by applying force across the eyes rather than the forehead, which prevents the user's chin from being pulled up too high.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A face mask, comprising:
an eye piece having a left side portion, right side portion, and a middle portion formed therebetween and being configured to extend around a user's nose, the left and right side portions each having a concavity formed therein and configured to be positioned around a user's eye;

a left side strap having a first terminal end mated to the left side portion of the eye piece and having a second terminal end, the left side strap having a left reusable cover;

a right side strap having a first terminal end mated to the right side portion of the eye piece and having a second terminal end, the right side strap having a right reusable cover; and a reusable adhesive coated onto at least a portion of the second terminal end of the left and right side straps such that the second terminal ends of the left and right side straps can be repeatedly and removably mated to a support structure;

wherein the left reusable cover has a first end and a second end, the first end of the left reusable cover being permanently attached to the left side strap between the reusable adhesive coating and the first terminal end of the left side strap;

wherein the right reusable cover has a first end and a second end, the first end of the right reusable cover being permanently attached to the right side strap between the reusable adhesive coating and the first terminal end of the right side strap; and wherein the left and right reusable covers are removably disposed over the reusable adhesive coating on each side strap.

2. The face mask of claim 1, wherein the left and right side straps are attached to the left and right side portions of the front eye piece along a central longitudinal axis extending centrally through the concavity in each of the left and right side portions such that the left and right side straps are configured to be aligned with a user's eyes when the left and right side portions are disposed over a user's eyes.

3. The face mask of claim 1, wherein the left and right side portions each have a substantially oblong region extending around a perimeter of the concavity, and each oblong region has a thickness that is greater than a thickness of the concavity.

4. The face mask of claim 1, wherein the front eye piece is formed from a compressible material.

5. The face mask of claim 1, wherein the concavity in each of the left and right side portions has an opening formed therein for allowing a user to see through the front eye piece.

6. The face mask of claim 1, wherein the middle portion of the front eye piece has a bridge portion formed therein and shaped to contour a human nose.

7. The face mask of claim 1, wherein the concavity extends in a forward direction relative to a front eye piece and the reusable adhesive is coated on a back side of each strap.

8. The face mask of claim 1, wherein each reusable cover comprises an elongate member, and the first ends of the left and right reusable covers are attached to the corresponding left and right side straps along linear fixations.

9. The face mask of claim 1, wherein each of the left and right reusable covers comprises a smooth releasable surface configured to contact the reusable adhesive coating.

10. The face mask of claim 1, wherein each of the left and right side straps has a length of about 10 inches and a width of about 0.75 inches, and the reusable adhesive coating on each of the left and right side straps covers about 3.5 inches by about 0.75 inches of each of the left and right side straps.

11. The face mask of claim 1, wherein the reusable adhesive coating comprises a low-tack pressure-sensitive adhesive.

12. A face mask, comprising:

a front eye piece sized to fit a human face;

left and right side straps, the side straps being attached to opposite left and right sides of the front eye piece, a reusable adhesive coating being formed on a back surface of an end of each side strap opposite to an end of each side strap attached to the front eye piece, and each side strap having a length that is greater than a length of the front eye piece such that the left and right side straps are configured to attach to corresponding sides of a seat headrest when a user is wearing the front eye piece and when a head of the user is positioned adjacent to the seat headrest; and left and right reusable covers, each reusable cover having first and second ends, the first end of the left reusable cover being permanently directly attached to the left side strap, the first end of the right reusable cover being permanently directly attached to the right side strap, the second end of each of the left and right reusable covers being removably attached to the reusable adhesive coating, and each reusable cover being removably disposed over the reusable adhesive coating.

13. The face mask of claim 12, wherein the front eye piece includes a left side portion having an oblong rim shaped to extend around a left eye of a human face, and a right side portion having an oblong rim shaped to extend around a right eye of a human face.

14. The face mask of claim 13, wherein the left and right side portions includes concavities formed therein, each concavity being surrounded by the oblong rim and each concavity having a depth sufficient to prevent contact between the concavity and a user's eye.

15. The face mask of claim 12, wherein the front eye piece bulges outward at a location of each eye on a human face.

16. The face mask of claim 12, wherein the front eye piece has openings at a location of each eye on a human face.

17. The face mask of claim 12, wherein the front eye piece has a mid-portion that is contoured to match a human nose.

18. The face mask of claim 12, wherein the first end of each of the left and right reusable covers is attached to the corresponding left or right side strap between the adhesive coating and the front eye piece such that the left and right reusable covers remain attached to the corresponding left and right side straps when the left and right reusable covers are not in contact with the reusable adhesive coating.

19. The face mask of claim 12, wherein each of the left and right reusable covers is rectangular, and the first end of each of the left and right reusable covers is attached to the corresponding left or right side strap by a linear fixation spanning a width of the corresponding left or right side strap.

20. The face mask of claim 12, wherein the reusable adhesive coating comprises elastomeric copolymer microspheres.

* * * * *